United States Patent
Kumar et al.

(10) Patent No.: US 7,396,671 B2
(45) Date of Patent: Jul. 8, 2008

(54) BIOTECHNOLOGICAL PROCESS FOR NEUTRALIZING ALKALINE BEVERAGE INDUSTRIAL WASTE WATER

(75) Inventors: Rita Kumar, Delhi (IN); Anil Kumar, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 284 days.

(21) Appl. No.: 11/024,023

(22) Filed: Dec. 28, 2004

(65) Prior Publication Data

US 2006/0141604 A1    Jun. 29, 2006

(51) Int. Cl.
*C12N 1/20* (2006.01)
(52) U.S. Cl. .................... 435/252.1; 424/93.4
(58) Field of Classification Search ........................ None
See application file for complete search history.

(56) References Cited

U.S. PATENT DOCUMENTS

2002/0064864 A1    5/2002    Kumar et al.

OTHER PUBLICATIONS

Yumoto et al.: "Exiguobacterium oxidotolerans sp. nov., a novel alkaliphile exhibiting high catalase activity" International Journal of Systematic and Evolutionary Microbiology, No. 54, Apr. 23, 2004, pp. 2013-2017.*

Collins et al., . Int. J. Syst. Bacteriol., 1984, 34, 91-92. [Chemotaxonomic study of an alklophilic bacterium, Exiguobacterium aurantiacum gen. nov., sp. nov. J. Gen. Microbiol., 1983, 129, 2037-2042.].*

Chaturvedi (P.) and Shivaji (S): Exiguobacterium indicum sp. nov., a psychrophilic bacterium, from the Hamta glacier of the Himalayan mountain ranges of India. Int. J. Syst. Evol. Microbiol., 2006, 56, 2765-2770.*

Yumoto, I. et al. "Exiguobacterium Oxidotolerants Sp. Nov., a Novel Alkaliphile Exhibiting High Catalase Activity" *International Journal of Systematic and Evolutionary Microbiology* 2004 vol. 54, pp. 2013-2017 XP-002347351.

Fruhling, A., et al. "Exiguobacterium Undae Sp. Nov. and Exiguobacterium Antarcticum Sp. Nov." *International Journal of Systematic and Evolutionary Microbiology* (2002) vol. 52, pp. pp. 1171-1176 XP009013832.

Ulukanli, Z., et al. "Alkaliphilic Micro-Organisms and Habitats" *Turk ish Journal of Biology* (2002) vol. 26, pp. 181-191 XP-002347352.

* cited by examiner

*Primary Examiner*—Irene Marx
(74) *Attorney, Agent, or Firm*—Ladas & Parry LLP

(57) ABSTRACT

The present invention provides a process of neutralizing beverage industrial wastewater by a bacterial strain *Exiguobacterium* sp. isolated in India, which strain is capable of bring down the pH of wastewater from 12.00 to 7.00 units within 1 to 1.5 hours.

2 Claims, No Drawings

US 7,396,671 B2

BIOTECHNOLOGICAL PROCESS FOR NEUTRALIZING ALKALINE BEVERAGE INDUSTRIAL WASTE WATER

FIELD OF THE INVENTION

The present invention relates to a bacterial isolate, *Exiguobacterium* sp. (MTCC 5183) deposited at International Depository IMTECH, Sector 39A, Chandigarh, India recognized by Budapest Treaty, More particularly, the present invention relates to a process of preparing bacterial isolate, *Exiguobacterium* sp., useful in neutralization of highly alkaline waste water from beverage industry deposited at International Depository IMTECH, Sector 39A, Chandigarh, India recognized by Budapest Treaty.

BACKGROUND AND PRIOR ART

Stringent laws and frequent checks by the authorities reflect environmental concerns now held by society. Thus, for insane now pH of wastewater of industries such as beverages may only deviate minimally from neutral point when discharged into a receiving watercourse or sewerage system. Various chemicals are available to neutralize the highly alkaline beverage industrial wastewater depending upon the application. In most cases, Sulfuric Acid ($H_2SO_4$) is used. The end user must consider the concentration to be used, must carefully analyze all the chemistries involved, must review manufacturers' warnings and instructions, and must consider common safety measures for hazardous liquids.

The process of treating wastewaters comprises treating with chemicals which can be either acids or bases or capable of forming acids or bases on addition to wastewater. Various chemicals are available for industrial neutralization depending upon the application and whether neutralization of an acidic or basic solution is being carried out.

The most commonly used neutralization chemicals for acid or base neutralization are 98% Sulfuric acid and 50% Sodium hydroxide. In many cases these are very good choices, however, there are many considerations when selecting chemicals and these may not always be the best selection.

The selection of the chemicals used for the neutralization of an acid or base is almost as important as the design of the neutralization system. Some of the major points to consider in the selection of chemicals are listed below:

Health and Safety.

Cost and Commence.

Physical Properties of neutralizing chemicals.

Storage Environment.

An explanation of chemical selectin criteria is as follows:

Health and Safety: Mixing of chemicals can lead to extreme hazardous or noxious reactions. For example: addition of any acid to cyanide bearing solution results in the release of deadly HCN gas.

Cost and Convenience: Most acids and bases work in most applications. Sulfuric acid ($H_2SO_4$), for example, is less costly and more potent than nitric acid. Concentration is also an important consideration in evaluating cost. Sulfuric acid, for example, can be purchased in concentration ranging from near 0% to 98%. Higher concentrations are generally less expensive.

Physical Properties: Physical properties of the selected reagent must be considered carefully. 50% Sodium hydroxide (NaOH), for example, begins to freeze at temperatures below 60° F. Decreasing the concentration to 25% eliminates this concern altogether, Hydrochloric acid (HCl), for example, out gasses severely. The gas is very highly corrosive and will attack all metallic objects. Therefore, if HCl is used it must be properly vented or used outdoors where the gasses can easily dissipate.

Storage Environment: Storage issues such as types of tanks and secondary containment available, familiarity of operators in handling hazardous chemicals, the dangers of refilling storage containers of procedures for transferring from bulk containers are of concern.

The most commonly used neutralizing chemicals are listed below:

Acids: Sulfuric Acid, Hydrochloric Acid, Nitric Acid, Phosphoric Acid and Carbon Dioxide which forms Carbonic Acid in water Bases: Sodium Hydroxide (Caustic Soda), Calcium Hydroxide, Calcium Carbonate (Lime or Limestone), and Ammonium Hydroxide Neutralization with Acids Sulfuric Acid is the most widely used and produced chemical in the world. Available in concentrations ranging from 0% to 98%, sulfuric acid is most economical of all and used universally for neutralization reactions. It is easier and safer to use than HCl or $HNO_3$ and is more potent than all of the other acids except for phosphoric acid. Sulfuric acid is typically used in concentrations ranging from 25% to 96%. However, 30% to 50% concentrations of sulfuric acid are generally recommended.

Hydrochloric Acid (HCl), also known as muriatic acid, is the second most commonly wed acid in industry (sulfuric acid being the first). It is very effective, and relatively inexpensive. At a maximum available concentration of 37%, HCl is about ⅓ as potent as sulfuric acid, thus making it relatively more expensive to use. Depending on temperature and agitation, HCl at concentrations above 10% evolves hydrogen chloride vapors which combine with water vapors present in the air. The gas thus formed is highly corrosive and attacks all metallic objects including building structures, sprinkler heads, copper wig, stainless steel, etc. Therefore, it must be properly vented or used outdoors where gasses can easily dissipate.

Nitric Acid ($HNO_3$) though a widely used chemical in many industries it does not enjoy the popularity of hydrochloric or sulfuric acid, as it is more expensive to use than either of them. Nitric acid evolves noxious gas which on combines with water vapors present in the air. The gas is highly corrosive and attacks all metallic objects including building structures, sprinkler heads, copper wiring, stainless steel, etc. Therefore, it must be properly vented or used outdoors where the gasses can easily dissipate.

Phosphoric Acid ($H_3PO_4$), very widely used in the production of agricultural fertilizer and detergent products it is a relatively inexpensive acid. However it still does not compete well with sulfuric and hydrochloric acid as it is a weak acid and does not fully disassociate in water at normal concentrations. This renders it safer to use compared to sulfuric or hydrochloric acid and the evolution of gasses is rare. It tends to buffer neutralization reactions and this makes for a slower reaction that is easier to control. Due to its cost (as compared to sulfuric acid) and availability, phosphoric acid is not commonly used in neutralization system.

Carbon Dioxide ($CO_2$), the third most concentrated gas found in earth's atmosphere, $CO_2$ is itself not an acid. It forms carbonic acid ($H_2CO_3$) when dissolved in water; and it is this carbonic acid that brings about the neutralization of alkalinity in solution. The most appealing feature of $CO_2$ is that it will not lower the pH of water below 7.0 (for all practical purposes). Additionally $CO_2$ is non corrosive, however as it is heavier than air and thus, asphyxiation is a hazard. Carbon dioxide is difficult to use and its use is limited because the gas must be dissolved into solution to be used. This requires the use of a carbonator, or some method to dissolve the gas into solution. Significant out-gassing also occurs, which does not hold a problem unless the process also requires the setting of solids. In cement pouring operations large amounts of alkaline wastewaters are generated. It is an excellent choice for such applications as the site is temporary, the gas is non-hazardous, can be used in-line assuming retention and mixing is considered and is self-buffering so regardless of dosage it will not lower the pH below 7.5-7.0.

Alkaliphiles

Several microorganisms exhibit more than one pH optimum for growth depend on growth conditions, particularly nutrients, metal ions, and temperature. The term "alkaliphile" is used for microorganisms that grow optimally or very well at pH values above 9. The first paper concerning an alkaline enzyme of alkaliphilic microorganisms was published in 1971. Over the past two decades, our studies have focused on the enzymology, physiology, ecology, taxonomy, molecular biology and genetics of alkaliphilic microorganisms. Industrial applications of these microorganisms have also been investigated extensively and some enzymes, such as alkaline proteases, alkaline amylases and alkaline cellulases, have been put to use on an industrial scale (Horikoshi. K. (1971) Production of alkline enzymes by alkalophilic microorganisms. Part 1. Alkaline protease produced by *Bacillus* No, 221. Agric. Biol. Chem. 36, 1407-1414, Horikoshi, K. and Akiba, T. (1982) Alkalophilic Microorganisms: A New Microbial World. Springer-Verlag, Heidelberg, Tokyo.)

Subsequently, many microbiologists have published numerous papers on alkaliphilic microorganisms in various fields. Cell surface of alkaliphiles can maintain the intracellular pH values neutral in alkaline environments of pH 10-13. In 1995, new host vector systems were developed by using alkaliphilic *Bacillus* C-125 mutants that are alkaline sensitive, and genes responsible for alkaliphily have been investigated (Horikoshi, K. (1991) Microorganisms in Alkaline Environments, Kodansha-VCH Tokyo, Weinheim, N.Y., Cambridge, Basel., Kudo, T., Hino, M. Kitada, M. and Horikoski, L (1990) DNA sequences required for the alkalophily of *Bacillus* sp. strain C-125 are located close top on its chromosomal DNA. J. Bacteriol. 172, 7282-7283.).

Although alkaliphiles have been used for a number of industrial applications but there is no research publication regarding the neutralization of beverage industrial wastewater using them. Some work on biological neutralization by a mix of bacteria in the presence of sugars has been considered for patenting and is disclosed in U.S. patent application Ser. No. 09/160,422, titled 'Microbial Composition and a Process Useful for the Neutralization of Alkaline Waste-Water'.

OBJECT OF THE INVENTION

The man object of the invention is to provide a bacterial isolate *Exiguobacterium* sp. (MTCC 5183) deposited at International Depository at IMTECH, Sector 39A, Chandigarh, India recognized by Budapest Treaty.

Another object of the invention is to provide a process for preparing a bacterial isolate *Exiguobacterium* sp. (MTCC 5183) deposited at International Depository at IMTECH Sector 39A, Chandigarh, India recognized by Budapest Treaty.

Another object of the invention is to isolate the bacterium *Exiguobacterium* sp. (MTCC 5183) deposited at International Depository at IMTECH, Sector 39A, Chandigarh, India record by Budapest Treaty which is useful to neutralize the highly alkaline waste water of beverage industry.

SUMMARY OF THE INVENTION

The present invention provides a bacterial isolate, *Exiguobacterium* sp. (MTCC 5183) deposited at International Depository at IMTECH Sector 39A, Chandigarh, India, as recognized by Budapest Treaty from beverage industrial waste water. This bacterial strain is capable to bring down the pH of waste water from 12.00-7.00 units within two hours. The neutralization of alkaline beverage industrial waste water by such buiotechnological process is highly effective and economical as compared to conventional neutralization process by chemical means.

Accordingly the present invention provides a bacterial isolate, *Exgiuobacterium* sp. (MTCC 5183), deposited at International Depository at IMTECH, Sector 39A, Chandigarh, India recognized by Budapest Treaty.

In one embodiment of the invention, the bacterial isolate is capable of growth in a medium of pH in the range of 10-12.00.

In another embodiment of the invention, the bacterial isolate is capable of lowering high pH of 12.0 to 11.5 of beverage industrial wastewater to neutral pH (7.5 to 7.00) within a period of 1-1.5 hours.

In another embodiment of the invention, the bacterial isolate is used to neutralize high pH (12.0 to 11.5) of beverage industrial wastewater to neutral pH (7.5 to 7.00) in ratio raging from 1:5-1:10.

In another embodiment of the invention, the bacterial isolate is obtained from activated sludge of an effluent treatment plant of local beverage industry located in Gaziabad, India.

In another embodiment of the invention, the bacterial isolate is Gram positive, non motile, rod shaped and oxidase negative.

In another embodiment of the invention, the bacterial isolate can hydrolyze starch.

In another embodiment of the invention, the bacterial isolate produces acids from glycerol cellobiose, D-mannose, mannitol, methyl α-D-glucoside, amygdalin and arbutin.

The present invention also provides a process for preparing a bacterium isolate of *Exiguobacterium* sp. (MTCC 5183) useful in neutralization of alkaline waste water of beverage industry having a pH in the range of 12.00-11.5, deposited at International Depository at IMTECH, Sector 39A, Chandigarh, India recognized by Budapest Treaty, the process comprising the steps of:

a) enriching activated sludge contaminated with bacteria by providing a sludge tact in alkaline baccilus medium, b) culturing the bacteria;

c) isolating the bacteria by centrifuging the culture obtained from step (b) after attaining the desired growth to obtain a pellet of bacterial cells;

d) dissolving the pellet obtained from step (c) it phosphate buffer;

e) neutralize alkaline wastewater of beverage industry having pH in the range of 12.00-11.5 by adding the bacterial pellet obtained from step (d) therein.

In one embodiment of the invention, the contaminated activated sludge is obtained from the pipe of an effluent treatment plant of a beverage industry located in Gaziabad, India.

In another embodiment of the invention, the enrichment of the sludge is effected for a period of 40-48 hours at 100-120 rpm at 33-35° C. in ratio of activated sludge to medium in the range of 1:5-1:10.

In another embodiment of the invention, the culturing of the bacteria is carried out in an alkaline baccilus medium and at a pH in the range of 11.00-12.00 and at 37 to 34° C.

In another embodiment of the invention, the bacteria is isolated by centrifuging the culture obtained from step (b) after attaining a growth evidenced by an optical density in the range of 1.5-2.0.

In another embodiment of the invention, enrichment of the sludge is carried out by ta 5-7 g of fresh activated sludge in am autoclaved flask containing 100-110 mi sludge extract, 50 µl Candid B (anti fungal) and alkaline baccilus medium.

In another embodiment of the invention, the sludge extract is prepared by centrifuging the sterilized sludge mixture at about 4000 rpm for about 20 min.

In another embodiment of the invention, the sterilized sludge mixture is prepared by dissolving activated sludge in distilled water in ratio ranges between 1:5-1:10 and autoclaving at about 15 psi for about one hour.

In another embodiment of the invention, the alkaline baccilus medium contains peptone, yeast exact, glucose, $K_2HPo_4$ and $Na_2CO_3$ in ratio about 1.0:0.5:1.0:0.1:1.0 by W/V.

In another embodiment of the invention, the ratio between the said sludge extract and the said alkaline baccilus medium is 1:5-1:10.

In another embodiment of the invention, the isolated bacterial isolate is cultured under defined conditions of media, temperature, pH and carbon source.

In another embodiment of the invention, the neutralizing capacity of all the bacterial isolates to lower the pH of beverage wastewater in a short period of time are determined.

In another embodiment of the invention, decrease in pH is monitored by pH meter.

In another embodiment of the invention, a bacterium is selected which is capable to lowering pH of alkaline beverage wastewater in a short period of about one hour.

In another embodiment of the invention, the selected bacterium is cultured under defined conditions by using alkaline baccilus medium followed by incubation at 32-37° C./80-120 rpm 8 hour for neutralizing the alkaline beverage industrial waste water.

In another embodiment of the invention, grown culture is centrifuged after attaining the heavy growth evidenced by optical density in the range of 2-2.5, In another embodiment of the invention, bacterial pellet is dissolved in phosphate buffer.

In another embodiment of the invention, neutralization of the highly alkaline wastewater of beverage industry was done by adding the bacterial pellet in wastewater to lower pH from 12.0-11.5 to 7.5-7.0 observed in 1 to 1.5 hours and determined by pH meter.

In another embodiment of the invention, the bacterium *Exiguobacterium* sp. is used as a whole cell.

DETAILED DESCRIPTION OF THE INVENTION

The present invention provides a bacterial isolate, *Exiguobacterium* sp. (MTCC 5183), deposited at International Depository at IMTECH, Sector 39A, Chandigarh, India recognized by Budapest Treaty. The bacterial isolate, *Exiguobacterium* sp. (MTCC 5183) deposited at International Depository at IMTECH, Sector 39A, Chandigarh, India recognized by Budapest Treaty, is capable of neutralizing highly alkaline waste water of beverage industry. The bacterial isolate is capable of growth in a medium of pH in the range of 10-12.00 and is also capable of lowering high pH of 12.0 to 11.5 of beverage industrial waste water to neutral pH (7.5 to 7.00) within very short period of 1-1.5 hours. The bacterial pellet is used to neutralize the high pH (12.0 to 11.5) of beverage industrial waste water to neutral pH (7.5 to 7.00) in ratio ranging from 1:5-1:10. The bacterial isolate is isolated from activated sludge of an effluent treatment plant of local beverage industry located in Gaziabad, India. It is observed that the isolate is Gram positive, non-motile, rod shaped and oxidase negative, hydrolyzes starch produces acids from glycerol, cellobiose, D-mannose, mannitol, methyl α-D-glucoside, amygdalin and arbutin.

The process of preparing the isolate of bacterium *Exiguobacterium* sp. (MTCC 5183), comprises the steps of:
(a) enriching the activated sludge contaminated with bacteria by providing a sludge elect in alkaline baccilus medium for the period of 40-48 hours at 100-120 rpm at 33-35° C. in ratio raging from 1:5-1:10;
(b) culturing the bacteria by using a said alkaline baccilus medium at pH 11.00-12.00 and at 37 to 34° C.;
(c) isolating the said bacteria by centrifuging the culture obtained from step (b) after attaining the heavy growth (O.D. 1.5-2.0) to obtain the pellet of bacterial cell;
(d) dissolving the pellet obtained from step (c) in phosphate buffer;
(e) neutralizing the alkaline wastewater (pH 12.00-11.5) of beverage industry by adding the bacterial pellet obtained from step (d) in waste water.

Enrichment of the sludge from said site is done by taking 5-7 g of fresh activated sludge in an autoclaved flask containing 100-110 ml sludge extract, 50 µl Candid B (anti fungal) and alkaline baccilus medium. The sludge extract is prepared by centrifuging the sterilized sludge mixture at about 4000 rpm for about 20 min. The sterilized sludge mixture is prepared by dissolving the activated sludge in distilled water in ratio ranges between 1:5-1:10 and autoclaved it at about 15 psi for about one hour. The alkaline baccilus medium contains peptone, yeast extract, glucose, $K_2HPo_4$ and $Na_2CO_3$ in ratio about 1.0:0.5:1.0:0.1:1.0 by W/V. A mixture of sludge extract and alkaline baccilus medium is used to entrap the maximum bacterial flora of the said site. The ratio between the said sludge extract and the said alkaline baccilus medium is 1:5-1:10. Isolated bacterial isolates are cultured under defined conditions such as media, temperature, pH, carbon source etc.

All the bacterial isolates (total two) are checked for their neutralizing capability to lower the pH of beverage wastewater in a short period of time. Decrease in pH is monitored by pH meter. A bacterium is selected which is capable to bring down the pH of alkaline beverage wastewater in a short period of about 1 hour. The selected bacterium is cultured under defined conditions using alkaline baccilus medium followed by incubation at 32-37° C./80-120 rpm 8 hour for neutralizing the alkaline beverage industrial wastewater. The grown culture is centrifuged after a the heavy growth O.D. (2-2.5) and then dissolved in phosphate buffer. Neutralization of the highly alkaline wastewater of beverage industry was done by adding the bacterial pellet in wastewater lowering of pH from 12.0-11.5 to 7.5-7.0 was observed in 1.5 h to one hour as checked by pH meter.

The bacterium *Exiguobacterium* sp. is used as a whole cell.

The bacterial stain concerned with the present invention is deposited at International Depository at IMTECH, Sector 39A, Chandigarh, India as recognized by Budapest Treaty.

| S. No. | Culture | MTCC ID No. |
|---|---|---|
| 1. | *Exiguobacterium* sp. (DSM ID 03-501) | MTCC 5183 |

The abovementioned bacterial strain exhibits a remarkable capability to neutralize highly alkaline beverage industrial wastewater within a short period of one hour under defied conditions. The bacterial strain of the invention has been isolated from six months old activated sludge from the ETP of a local beverage industry. To isolate a potential bacterial isolate, 10 g activated sludge from the said site was added in the 500 ml autoclaved flask containing 100 ml activated sludge extract 100 ml alkaline *bacillus* medium and 50 ul Candid B (anti-fungal). Alkaline *bacillus* medium contained 1 gm peptone, 0.5 gm yeast extract, 1 g glucose, 0.1 g $K_2HPO_4$ and 1 g $Na_2CO_3$. Peptone and yeast en were autoclaved at 15 psi while glucose, $K_2HPo_4$ and $Na_2CO_3$ were autoclaved at 10 psi. After autoclaving the different ingredients at different psi, all the ingredients are mixed together aseptically. The enrichment flask was kept at 100 rpm for 48 hours at 35° C.

For the preparation of activated sludge extract, 1 kg activated sludge was taken and dried at 50° C. for 2 hour. 400 g of dried activated sludge was dissolved in 960 ml single distilled water and autoclaved at 15 lbs for 1 hour. After autoclaving, the sample was centrifuged at 5000 rpm for 10 minutes. The supernatant (extract) was collected and stored in sterile bottle for the preparation of enrichment flask and further use.

The enriched activated sludge sample was serially diluted in 0.85% saline. 100 ul from each respective dilution was spread ont agar petri plates contain activated sludge extract and 50% ABM. AMB contained peptone, yeast extract, glucose, $K_2HPo_4$, $Na_2CO_3$ and 2% agar. Peptone and yeast extract were autoclaved at 15 psi while glucose, $K_2HPo_4$ and $Na_2CO_3$ were autoclaved at 10 psi. After autoclaving the different ingredients at different psi, all the ingredients are mixed together aseptically. The plates thus obtained were incubated at 35±2° C. for 24-96 hrs in inverted position.

On the basis of colony morphology and color, total 2 bacterial isolates were selected to check their capability for neutralizing the alkaline wastewater. The single isolated colonies were picked and streaked on fresh plates coding the same medium. The above step was repeated till pure colonies were obtained.

To check the neutralizing capability of the two isolated bacteria, 200 ml beverage industrial wastewater of high pH (12.00) was taken in 500 ml glass flask at two places and each bacterial growth was added individually. Decrease in pH was monitored by a pH meter.

Out of two, only one isolate was found capable to grow on high pH (12.00) and bring down the pH of wastewater within a short period of 2 hour. This bacterium was identified as *Exiguobacterium* sp. (DSM ID 03-501) and the main characteristic features are:

This bacterium, *Exiguobacterium* sp. MTCC 5183 (DSM ID 03-501), is facultative aerobic in nature, is gram positive, is non-motile, is oxidase negative, shows optimum growth at 35° C. and is also capable of growth in a high pH environment of pH 12.0 to 11.5, can hydrolyze starch as well as produce acids from glycerol, cellobiose, D-mannose, mannitol, methyl α-D-glucoside, amygdalin and arbutin.

In a neutralization experiment, beverage industrial wastewater was taken from a local beverage industry. The bacterium *Exguobacterium* sp. (MTCC 5183), as screened above, was inoculated in 200 ml ABM. The culture was incubated at 35° C. for 8 hour under shaking conditions (100-120 rpm). After observing the heavy bacterial growth (O.D.=2), the culture was centrifuged at 7,000 rpm at 4° C. The culture pellet was dissolved in 20 ml phosphate buffer (0.05M, pH 6.8). This pellet was added in a flask containing 200 ml beverage industrial waste water (pH −12.00). The flask was kept at under shaking conditions (100-120 rpm). Decrease in pH was observed just after 2 hour. This bacterium, *Exiguobacterium* sp. MTCC 5183 (DSM ID 03-501) has been capable to bring down the pH from 12.0-11.5 to pH 7.7-7 within a short period of 1.5 h to one hour. PH was monitored by a ph meter.

The invention further provides a process for the preparation of bacterial growth useful in neutralizing the alkaline wastewater:

a) enriching the activated sludge of the said site using activated sludge extract and AMB to isolate the bacteria having neutralization capability;

b) using the mixture of activated sludge extract and alkaline *bacillus* medium (1 gm peptone, 0.5 gm yeast extract, 1 g glucose, 0.1 g $K_2HPO_4$ and 1 g $Na_2CO_3$ for 100 ml) to entrap the desired potential bacteria from the said site;

c) culturing the said bacteria isolated from specific site under defined conditions such as media, temperature, pH, carbon source etc.;

d) checking the neutralizing capability of isolated bacterial isolates by inoculating them in alkaline beverage industrial waste water, e) decrease in pH was monitored by a pH meter;

f) selecting a bacterial isolate which can neutralize alkaline waste water in a short time;

g) cultering the selected bacterium under defined conditions for neutralizing the alkaline beverage industrial wastewater. ABM was used to grow the culture. The culture flask was incubated at 35° C./120 rpm 8 hour in order to obtain heavy growth;

h) centrifuging the resulting culture after attaining the heavy growth O.D. (2.00);

i) collecting the bacterial pellet and dissolving in phosphate buffer (0.05M, pH 6.8);

j) neutralizing the highly alkaline wastewater of beverage industry by adding the bacterial pellet in 200 ml wastewater. Lowing of pH from 12.0-11.5 to 7.5-7.00 was observed in one hour as checked by pH meter.

The following examples are given by way of illustration and therefore should not be construed to limit the scope of the invention.

EXAMPLE 1

In an endeavor of exploring alkaliphilic bacteria, strategic isolation was done to entrap the potential bacterial flora from the specific site. Bacteria were isolated from six months old activated sludge from the ETP of a local beverage industry To isolate a potential bacterial isolate, 5 g activated sludge from the said site was added in the 500 ml autoclaved flask containing 100 ml activated sludge extract, 100 ml alkaline *bacillus* medium and 50 ul Candid B (anti gal). Alkaline *bacillus* medium contained 1 gm peptone, 0.5 gm yeast extract, 1 g glucose, 0.1 g $K_2HPO_4$ and 1 g $Na_2CO_3$. Peptone and yeast extract were autoclaved at 15 psi while glucose, $K_2HPO_4$ and $Na_2CO_3$ were autoclaved at 10 psi. After autoclaving the different ingredients at different psi all the ingredients are mixed together aseptically. The enrichment flask was kept at 120 rpm for 96 hour at 35° C. For the preparation of activated sludge extract, 1 Kg activated sludge was taken and dried at 50° C. for 2 hour. 400 g of dried activated sludge was dissolved in 960 ml single distilled water and autoclaved at 15 lbs for 1 hour. After autoclaving, the sample was centrifuged at 5000 rpm for 10 minutes. The supernatant (extract) was collected and stored in sterile bottle for preparation of enrichment flask and further use. Enriched activated sludge sample was serially diluted in 0.85% saline. 100 ul from each respective dilution was spread onto agar petri plates containing activated sludge extract and 50% ABM. AMB contained peptone, yeast extract, glucose, $K_2HPO_4$, $Na_2CO_3$ and 2% agar. Peptone and yeast extract were autoclaved at 15 psi while glucose, $K_2HPO_4$ and $Na_2CO_3$ were autoclaved at 10 psi. After autoclaving different ingredients at different psi, all ingredients are mixed together aseptically. Plates thus obtained were incubated at 35±2° C. for 24-96 hrs in inverted position.

On the basis of colony morphology and color, total 2 bacterial isolates were selected to check their capability for the alkaline wastewater. The single isolated colonies were picked and streaked on fresh plates containing the same medium. The above step was repeated till pure colonies were obtained.

EXAMPLE 2

In order to explore the potential bacteria for neutralization of alkaline beverage industrial wastewater, total two bacteria were isolated from the pipe through which beverage industrial wastewater has been passed over a period of long time. Theses bacterial isolates were selected to check their capability for neutralizing the alkaline waste water. The single isolated colonies were picked and streaked on fresh plates containing the same medium. The above step was repeated tiff pure colonies were obtained. To check neutralizing capability of two isolated bacteria, 200 ml beverage industrial wastewater of high pH (12.00) was taken in 500 ml glass flask at two places and each bacterial growth was added individually. Decrease in pH was monitored by pH meter (Table 1). Out of two, only one isolate was found capable to grow on high pH (12.00) and bring down the pH of wastewater within a short period of 2 hour. This bacterium was identified as *Exiguobacterim* sp. (DSM ID 03-501) and the main characteristic features are:

*Exiguobacterium* sp. (DSM ID) 03-501), is facultative aerobic in nature, gram positive, is non-motile, is oxidase negative, shows optimum growth at 35° C., is capable of growth at high pH environment (pH 12.00), is capable of hydrolyzing starch and produces acids from glycerol, cellobiose, D-mannose, mannitol, methyl α-D-glucoside, amygdalin and arbutin.

EXAMPLE 3

In order to explore the potential bacteria for neutralization of alkaline beverage industrial wastewater, total two bacteria were isolated from the activated sludge of a beverage industrial ETP. Theses bacterial isolates were selected to check their capability for neutralizing the alkaline waste water. The single isolated colonies were picked and streaked on fresh plates containing the same medium. The above step was repeated till pure colonies were obtained. To check the neutralizing capability of the two isolated bacteria, 200 ml beverage industrial wastewater of high pH (12.00) was taken in 500 ml glass flask at two places and each bacterial growth was added individually. Decrease in pH was monitored by a pH meter (Table 1).

TABLE 1 pH reduction of alkaline wastewater by isolated alkaliphilic bacteria

| Bacterial Isolates | Reduction in pH of waste water during course of time | | | | |
|---|---|---|---|---|---|
| | 0 hr | 0.5 hr | 1.0 hr | 1.5 hr | 2.0 hr |
| Isolate 1 | 12.10 | 12.10 | 12.00 | 11.87 | 11.66 |
| Isolate 2 (*Exiguobacterium* sp) | 12.10 | 8.33 | 7.10 | 7.06 | 7.04 |

EXAMPLE 4

In order to observe the growth of screened bacterium, *Exiguobacterium* sp. on a suitable medium, two loops from agar plate of *Exiguobacterium* sp. were streaked onto plates of NB (Nutrient broth) medium and ABM. Alkaline *bacillus* medium contained 1 gm peptone, 0.5 gm yeast exact, 1 g glucose, 0.1 g $K_2HPO_4$ and 1 g $Na_2CO_3$. Peptone and yeast extract were autoclaved at 15 psi while glucose, $K_2HPO_4$ and $Na_2CO_3$ were autoclaved at 10 psi. After autoclaving the different ingredients at different psi, all the ingredients are mixed together aseptically. The plates thus obtained were incubated at 35±2° C. for 24-96 hrs in inverted position.

NB medium containing 2% agar was having original pH about 7 while ABM medium was having original pH 10.5. For increasing the pH of media, Tris-HCL and $Na_2CO_3$—$NaHCO_3$ buffer were used.

TABLE 2 growth of *Exiguobacterium* sp. on NB and ABM medium

| pH values | NB medium | ABM medium |
|---|---|---|
| 7.00 | + | + |
| 8.00 | + | ++ |
| 9.00 | ++ | +++ |
| 10.00 | − | ++++ |
| 11.00 | − | ++++ |
| 12.00 | − | +++++ |

+ Very poor growth; ++ Poor growth; +++ Good growth; ++++ Very good growth

It was observed that ABM medium of high pH is a suitable medium to grow the *Exiguobacterium* sp.

EXAMPLE 5

Alkaline beverage wastewater was neutralized with with lyophilize powder of *Exiguobacterium* sp. Bacterial pellet of 40 ml culture (O.D.=2.00) was lyopilized and added to 500 ml flask containing 200 ml alkaline beverage wastewater. Inoculated flask was kept at 35° C. for one hr. Decrease in pH was observed within one hour (Table 3.)

TABLE 3 pH reduction of alkaline wastewater by lyophilized bacterial powder of *Exiguobacterium* sp.

| Bacterium | Reduction in pH of waste water during course of time | | | | |
|---|---|---|---|---|---|
| | 0 hr | 0.5 hr | 1.0 hr | 1.5 hr | 2.0 hr |
| *Exiguobacterium* sp. (Set 1) | 12.10 | 8.43 | 7.09 | 7.04 | 7.03 |
| *Exiguobacterium* sp. (Set 2) | 12.10 | 8.77 | 7.05 | 7.03 | 7.01 |

ADVANTAGES

1. The neutralization of alkaine beverage wastewater using *Exiguobacterium* sp. is an economical and effective process. In conventional acid-neutralization process, tones of acid are used for the neutralization while in the developed biological process decrease the cost drastically.

2. The neutralization of alkaline beverage wastewater by biological mean is quite safe process as the utilization of acid in large quantities for the neutralization of wastewaters is not safe for the industry as the strong acid has dangerous effect on the health of workers as well as on the industrial processes. Besides this, use of large quantity of acid also increases the volume of industrial wastewaters to be drained out in the main stream.

We claim:

1. A biologically pure culture of the strain *Exiguobacterium* sp., identification number MTCC 5183, deposited at International Depository at IMTECH, Sector 39A, Chandigarh, India, said strain being capable of growth in a medium with a pH in the range of 10-12.00 and being capable of lowering a pH of 12.0 to 11.5 of beverage industrial wastewater to a neutral pH of 7.5 to 7.00 within a period of 1-1.5 hours, said strain being Gram positive, non motile, rod shaped and oxidase negative, and being capable of hydrolyzing starch and producing acids from glycerol cellobiose, D-mannose, mannitol, methyl .alpha.-D-glucoside, amygdalin and arbutin.

2. The strain as claimed in claim 1, wherein the strain is obtained from activated sludge of an effluent treatment plant of beverage industry located in Gaziabad, India.

* * * * *